United States Patent
Jackson et al.

(10) Patent No.: US 9,120,739 B2
(45) Date of Patent: Sep. 1, 2015

(54) METHOD AND APPARATUS FOR ESTERIFYING FATTY ACID

(75) Inventors: Richard David Jackson, Hertfordshire (GB); Owen Matthew Davies, Milton Keynes (GB)

(73) Assignee: Renewable Holdings Limited, Kingston Upon Thames (GB)

( * ) Notice: Subject to any disclaimer, the term of this patent is extended or adjusted under 35 U.S.C. 154(b) by 356 days.

(21) Appl. No.: 13/577,578

(22) PCT Filed: Feb. 7, 2011

(86) PCT No.: PCT/GB2011/000158
§ 371 (c)(1), (2), (4) Date: Oct. 8, 2012

(87) PCT Pub. No.: WO2011/095786
PCT Pub. Date: Aug. 11, 2011

(65) Prior Publication Data
US 2013/0030205 A1    Jan. 31, 2013

(30) Foreign Application Priority Data
Feb. 8, 2010 (GB) .................................. 1001984.2

(51) Int. Cl.
*C11C 3/00* (2006.01)
*B01J 19/18* (2006.01)
(Continued)

(52) U.S. Cl.
CPC ................ *C07C 67/08* (2013.01); *C10L 1/026* (2013.01); *C11C 3/003* (2013.01); *C10G 2300/1011* (2013.01); *C10G 2300/4075* (2013.01);
(Continued)

(58) Field of Classification Search
CPC ........ C07C 67/03; C07C 67/08; C11C 3/003; Y02E 50/13; C10L 1/026; B01J 19/18; B01J 3/04; B01J 2219/00094; B01J 2219/00162; B01J 2219/185
See application file for complete search history.

(56) References Cited

U.S. PATENT DOCUMENTS 3,091,518 A * 5/1963 Burke, Jr. et al. ............. 422/135
2006/0224005 A1* 10/2006 Felly ............................ 554/174
(Continued)

FOREIGN PATENT DOCUMENTS

EP    2 081 675    7/2009
GB    864069        3/1961
(Continued)

OTHER PUBLICATIONS

Chongkhong S et al: "Continuous esterification for biodiesel production from palm fatty acid distillate using economical process", Renewable Energy, Pergamon Press, Oxford, GB, vol. 34, No. 4, Apr. 1, 2009, pp. 1059-1063.*

(Continued)

*Primary Examiner* — Deborah D Carr
(74) *Attorney, Agent, or Firm* — Fay Sharpe LLP (57) ABSTRACT

A method of esterifying free fatty acid in natural oil comprises heating the natural oil (2) to a first temperature above a reaction temperature, feeding the heated natural oil into an acid-resistant pipe reactor (5), providing a mixture of acid catalyst (6) and short chain alcohol (8) at a second temperature below the reaction temperature, and feeding the mixture of acid catalyst and short chain alcohol into the natural oil in the pipe reactor (5). The short chain alcohol and free fatty acid react at the reaction temperature to form an ester.

23 Claims, 3 Drawing Sheets

(51) Int. Cl.
*C07C 67/08* (2006.01)
*C10L 1/02* (2006.01)

(52) U.S. Cl.
CPC ... *C10L2200/0476* (2013.01); *C10L 2290/141* (2013.01); *C10L 2290/54* (2013.01); *C10L 2290/56* (2013.01); *Y02E 50/13* (2013.01)

(56) References Cited

U.S. PATENT DOCUMENTS

2008/0051593 A1 2/2008 Berry et al.
2009/0247785 A1* 10/2009 Parnas et al. .................. 562/512
2010/0025607 A1 2/2010 Tsung

FOREIGN PATENT DOCUMENTS

| GB | 864069 | A | * | 3/1961 |
| GB | 1 284 870 | | | 9/1972 |
| GB | 1284870 | A | * | 8/1981 |
| GB | 2 161 809 | | | 1/1986 |
| GB | 2161809 | A | * | 1/1986 |
| WO | WO 2008/024716 | | | 2/2008 |
| WO | WO 2008024716 | A2 | * | 2/2008 |

OTHER PUBLICATIONS

International Search Report mailed May 20, 2011 for International Application No. PCT/GB2011/000158.

International Preliminary Report on Patentability with Written Opinion mailed May 20, 2011 for International Application No. PCT/GB2011/000158.

Chongknong, S., et al., "Continuous esterification for biodiesel production from palm fatty acid distillate using economical process", Elsevier, Renewable Energy 34 (2009) pp. 1059-1063.

* cited by examiner

METHOD AND APPARATUS FOR ESTERIFYING FATTY ACID

The present invention relates to a method and apparatus for esterifying fatty acid in a method for the synthesis of biodiesel.

Biodiesel is manufactured by transesterification of animal or vegetable oils/fats. Such oils and fats comprise triglyceride esters containing long chain fatty acid moieties. In biodiesel synthesis, such triglycerides are transesterified with short chain alcohols, typically methanol and sometimes ethanol though other alcohols have been used. The reaction can be carried out in the presence of an acidic or basic catalyst and in general the basic catalysts are faster, with sodium hydroxide or potassium hydroxide being the most common. Typically, sodium hydroxide or potassium hydroxide with relatively low water level (particularly in powder or pellet form) is mixed with the alcohol, for example methanol, and then mixed with the oil. Typically, the oils or fats also include a certain amount of long chain fatty acid present as free fatty acid, rather than as the ester. The presence of such free fatty acid is a problem when a basic catalyst is used, because the base will typically form soap with the free fatty acids, and liberate water. Both of these are impurities which decrease the quality of the biodiesel produced. It is therefore desired to remove free fatty acid from the natural oil before transesterification takes place.

It is known to remove free fatty acid by esterifying it using a short chain alcohol. The esterification of the free fatty acid generates a short chain alcohol ester which is biodiesel. This increases the yield of biodiesel and, at the same time, removes the problematic free fatty acid.

Typically, this reaction can be catalysed by an acid catalyst.

The speed of the reaction depends on the reaction temperature and increases rapidly as the reaction temperature increases. However, there is a problem in that hot acidic liquids are extremely corrosive. Normally the reaction can only be carried out at high reaction temperatures (above about 70 C) if components contacting the liquid are made of very high specification acid resistant steels, such as hastelloy, or are provided with protective linings, for example of PTFE. However, these high specification steels are extremely expensive and some complex components such as pumps and valves cannot readily be provided with protective linings. It is therefore very difficult to design a system for esterifying fatty acid in natural oil, that can operate at a high reaction temperature and is not extremely expensive.

An object of the present invention is to provide a method and apparatus for esterifying fatty acid in natural oil, in which at least some of the aforesaid problems are mitigated.

The present invention in based on the realisation that the heating and acidifying steps can effectively be kept separate. That is, the natural oil can be heated to a temperature above the reaction temperature before the acid catalyst is added. Hot natural oil does not have high corrosivity and can be fed through conventional equipment. The acid catalyst is not required in great quantities. Acid catalyst which is not heated can be supplied and mixed in the reactor with the natural oil. As there is much more natural oil than acid catalyst, the temperature is reduced only slightly by adding the relatively cold acid. Therefore by heating the oil to slightly above the reaction temperature and then adding the cold acid catalyst, the mixture can be brought to the required reaction temperature without directly heating the acid catalyst.

The reactor can be a simple pipe reactor that is lined with an acid-resistant material such as PTFE. Valves and pumps upstream of the reactor do not need to be made of material that is capable of resisting high temperature acid, as they will be in contact with either hot oil or cold acid.

Accordingly, the present invention provides a method of esterifying free fatty acid in natural oil, comprising heating the natural oil to a first temperature above a reaction temperature, feeding the heated natural oil into an acid-resistant pipe reactor, providing a mixture of acid catalyst and short chain alcohol at a second temperature below the reaction temperature, and feeding the mixture of acid catalyst and short chain alcohol into the natural oil in the pipe reactor to cause the short chain alcohol and free fatty acid to react at the reaction temperature to form an ester.

Advantageously, the reaction temperature is in the range 100° C. to 200° C., preferably 120° C. to 170° C.

Advantageously, the first temperature is higher than the reaction temperature by a temperature difference in the range 10° C. to 50° C., preferably 20° C. to 40° C.

Advantageously, the second temperature is less than 70° C., preferably less than 60° C.

Advantageously, the mixture of acid catalyst and short chain alcohol is fed into the natural oil in the pipe reactor at a pressure greater than 0.5 bar gauge, preferably in the range 1 to 20 bar gauge.

Advantageously, the mixture of acid catalyst and short chain alcohol is fed into the natural oil in the pipe reactor at an angle to the direction of flow of the natural oil.

Advantageously, the method includes reducing the pressure of reactants at an outlet of the pipe reactor.

The present invention further provides an apparatus for esterifying free fatty acid in natural oil, comprising a heater for heating natural oil to a first temperature above a reaction temperature, a feed for feeding the heated natural oil into an acid-resistant pipe reactor, a feed for a mixture of acid catalyst and short chain alcohol at a second temperature below the reaction temperature, the feed for the mixture of acid catalyst and short chain alcohol being configured to feed the mixture into the natural oil in the pipe reactor to cause the short chain alcohol and free fatty acid to react at the reaction temperature to form an ester.

Advantageously, the apparatus includes a pressure reducing valve for reducing the pressure of reactants at an outlet of the pipe reactor.

Advantageously, the pipe reactor includes a corrosion-resistant lining.

Preferred and optional features of the present invention will be described further below.

The natural oils used in the present invention may comprise fats, oils or mixtures thereof obtained from natural sources such as animal or vegetable sources Such fats and oils comprise triglyceride esters having at least one relatively long chain carboxylate moiety (for example, but not limited to, having from 12 to 22 carbon atoms). Such materials are very well known to the person skilled in the art.

The natural oils may have been treated by any suitable pre-treatment process, for example de-gumming.

The natural oil is suitably heated to a temperature which is above 100° C., preferably above 120° C., and preferably below 200° C., most preferably below 170° C.

The short chain alcohol may comprise any suitable short chain alcohol, for example a C1-C4 alcohol, straight or (where appropriate) branched. Preferably, it is methanol or ethanol, most preferably methanol.

The acid catalyst preferably comprises a mineral acid, such as hydrochloric or sulphuric acid preferably sulphuric acid, which is supplied in liquid form as an aqueous solution.

The relative quantities of the reactants can be at any suitable level. Preferably, the ratio by mass of short chain alcohol to free fatty acid content of the natural oil is in the range 1:1 to 1:20, more preferably 1:1 to 1:6, most preferably in the range 1:1 to 1:4.

It is preferable to have a substantial excess of short chain alcohol over free fatty acid. This is to ensure that the reaction is stoichiometrically driven towards completion.

The content of free fatty acid in the natural oil is typically in the range 1-20%, but can up to 70% or even higher for acid oils of 100% free fatty acids.

The ratio by mass of acid catalyst to natural oil is suitably in the range 0.01%-5%.

Preferably, the acid catalyst and the short chain alcohol are mixed before being mixed with the natural oil.

The skilled person will be able to provide mixing devices (comprising pumps, valves, etc) which can mix and transport the acid catalyst and the mixture of acid catalyst and short chain alcohol.

Preferably, prior to mixing, the acid catalyst and the mixture of acid catalyst and short chain alcohol are at a temperature below the reaction temperature. They should be at a temperature below that at which the feed device will undergo significant corrosion. Preferably, they are substantially at ambient temperature or below ambient temperature. Ambient temperature here means a temperature at which the acid catalyst and short chain alcohol exist if no active heating step has been carried out. They may be cooled if necessary.

The feeds for the reactants may comprise any suitable feeds, for example they may comprise pumps. They may comprise storage means such as tanks.

If the temperature of the acid catalyst or the mixture of acid catalyst and short chain alcohol is below about 70° C., it is not highly corrosive. Therefore, if it is at ambient temperature, materials such as conventional engineering stainless steel can usually be used.

The tanks may comprise simple structural materials, such as steel, stainless steel or polypropylene.

The pipe reactor may comprise any suitable design of reactor. It should have an inflow end and an outflow end, a flow direction being defined from the inflow end to the outflow end.

The reactor may have any suitable internal configuration. Preferably, it is substantially parallel sided, though the flow cross section may vary across the length of the pipe reactor. Means may be provided for heating or cooling the pipe reactor.

The pipe reactor has the advantage that it can be operated continuously, which can offer higher treatment rates and simpler control than a batch process.

The pipe reactor may have a diameter in the range 2-1600 mm, preferably 12-500 mm. More preferably, the diameter is 130 mm or more.

The pipe reactor can be constructed as single length of pipe or a plurality of lengths of pipe connected together. It may have a substantially straight configuration or it may be curved. It may comprise bends or turns. A plurality of straight pipe sections connected by U-bends may be provided, to provide a compact structure. The pipe reactor may comprise a plurality of substantially straight pipe sections connected by headers. The straight line pipe sections may be contained within a single structure, for example an insulated structure or a vessel for containing heated fluid for heating the pipe reactor.

Where the pipe reactor passes through a heat exchanger, it may be the same heat exchanger as is used to initially heat the oil before the oil is fed into the pipe reactor.

The total length of the pipe reactor should be sufficient to achieve the desired degree of conversion of free fatty acid to biodiesel. The length is typically in (but not limited to) the range 5-100 meters, preferably 10-30 meters.

The pipe reactor must have a sufficient degree of acid resistance to have a reasonable working life. It should also be capable of containing the mixture at the chosen operating pressure, which is typically in the range 1-20 bar gauge. This may be obtained by using a simple structural steel pipe lined with an acid resistant lining such as a PTFE lining.

Any suitable volume flow rate may be used, depending upon the desired throughput of material.

Preferably, reactants flow through the reactor in one direction in the sense that the flow is not an oscillating flow. That is, steps are not taken to actively cause the flow to change direction. The flow direction referred to here is the bulk flow direction. In the apparatus of the invention, a pump or pumps may be provided for driving flow through the reactor, the pumps being normally operated in one direction.

The reactants are preferably placed under a pressure in excess of 0.5 bar gauge, more preferably in the range 1-20 bar gauge.

The reactants may be passed from the pipe reactor to any suitable means, for example to a separator for separating excess short chain alcohol from the natural oil.

Where the reactants are placed under pressure, they may be passed through a pressure reducing valve into a vessel. Due to the reduction in pressure, the excess short chain alcohol will be substantially completely removed by evaporation. The natural oil from which the alcohol has been removed may then be fed, for example by a pump or other feed device, to a further processing stage, for example to transesterification. Further heating may be required to replace the heat lost by the vaporisation of the short chain alcohol. Vaporised short chain alcohol may be collected and condensed. The heat of condensation of the alcohol vapour may be used to heat the natural oil that is initially fed in at ambient temperature. The condensed alcohol may be reused after drying.

In the present invention, it is found that mixing means are not normally required in the pipe reactor, because the mixture of acid catalyst and short chain alcohol is typically easily dispersed within the natural oil. The feed for the mixture of short chain alcohol and acid catalyst may be configured to introduce a sufficient degree of initial mixing to disperse the reactants. For example, the feed may comprise a jet nozzle and it may be configured to feed the mixture of short chain alcohol and acid catalyst at an angle to the bulk flow direction through the pipe reactor. Additional mixing means may be provided if necessary, for example static mixer elements. Where these are present, they may be made of a material which is acid resistant or treated with an acid resistant layer, such as PTFE. A high shear rotor/stator mixing device may be provided.

It is not normally necessary to separate the alcohol ester of fatty acid from the rest of the natural oil at this stage in the process. Typically, the treated mixture of natural oil and ester is passed to an apparatus for the synthesis of biodiesel by transesterification of the natural oil. Separation of short chain alcohol ester from glycerine formed in the transesterification reaction normally occurs downstream of such a transesterification apparatus.

Preferably, the flow within the pipe reactor is substantially plug flow. This has the advantage that there is a greater degree of mixing in the direction normal to the bulk flow direction than there is parallel to the bulk flow direction. This helps to prevent reactants that have reacted from diluting the unreacted reactants. Plug flow may be enhanced by the use of static mixers that are configured to provide a greater degree of mixing in the direction normal to the bulk flow direction than in the direction parallel to the bulk flow direction, or any other baffling type device that maintains plug flow and good temperature distribution.

An alkaline material may be added to the natural oil after the esterification process in order to neutralise the acid catalyst. For example, a methanolic solution of sodium methalte may be used. The alkaline neutralising agent may be added in a final stage of the pipe reactor or in a separate treatment. The neutralised acid and alkali will then form a polar phase that will separate naturally from the natural oil, being immiscible therewith, and can be removed before being fed to further stages in the process, such as the transesterification step.

The method and apparatus of the present invention preferably form part of a process for producing biodiesel from a fuel crop. Such a process typically comprises the following steps:

a) The fuel crop, typically in the form of seed or nuts, is received. Optionally, it is treated by washing, cleaning, grading, removal of foreign objects etc.

b) Seeds or nuts are crushed. This may be carried out in one or more steps in apparatus known to the person skilled in the art. The natural oil is obtained from the crushed seeds or nuts, for example by pressing.

c) Hexane treatment. This is to remove toxic or noxious materials. The person skilled in the art will be aware of suitable techniques for hexane treatment. Suitably, hexane is recycled.

d) Degumming. This is the process whereby phospholipids typically obtained from the shell material of the seeds or nuts are removed. Typically, the oil is heated to a reaction temperature that is suitably in the range 80-150° C., more preferably around 90-120° C. It is then reacted with phosphoric acid, which polymerises phospholipids to form solids, which are then separated by gravity. Treated oil is removed from the top of the separation tank. Separated polymerised phospholipids are removed from the bottom of the tank and disposed of. They may for example be burnt. Heat released by burning may be used to heat the process.

f) Esterification of free fatty acid according to the present invention.

g) Separation of excess short chain alcohol. Excess short chain alcohol is suitably removed by evaporation.

h) biodiesel synthesis by transesterification.

i) Separation of biodiesel. Separation may be achieved by any conventional means, for example, by gravity separation, by centrifuging or by cyclone.

Glycerine separated from the biodiesel may be disposed of by any suitable means, for example it may be burnt to provide heat for the processes described above.

Preferably, the apparatus of the present invention comprises part of a plant that comprises either an apparatus for degumming the natural oil or an apparatus for synthesis of biodiesel, or preferably both.

The apparatus preferably includes a heater for heating natural oil that is fed to the degumming apparatus or the apparatus for esterifying free fatty acid.

Where a degumming apparatus is present, the natural oil is preferably passed through the degumming apparatus before esterifying the free fatty acid.

Preferably, there is a feed, for example a pipe, from the degumming apparatus to the apparatus for esterifying free fatty acid, or from the apparatus for esterifying free fatty acid to a transesterification apparatus. Preferably, there is no intermediate cooling step in which the temperature drops close to ambient temperature. In this way, heat energy delivered to the natural oil at the beginning of the process can be retained in the plant, reducing the heat energy requirement of the apparatus.

It should be noted that, where free fatty acid is reacted into methylester after the step of esterifying free fatty acid, the natural oil may cool by removal of the latent heat of vaporisation of the short chain alcohol. However, this is not designed as a cooling step. Further, the temperature of the natural oil is not usually reduced by this step to ambient temperature.

The transesterification reaction carried out in step h) may be substantially improved as described in our European patent application EP2081675A. The method and apparatus described therein are intended to overcome the problem that basic methanol and oil do not mix very well, because of their different densities and because of the coalescing nature of their respective phases. Conventional approaches to improving kinetics of transesterification have included raising the temperature and applying a large degree of shear by agitation. The inventors seek to provide the required degree of mixing within a pipe reactor, which is preferable because it can provide a continuous reactor, enabling higher throughput and efficiency.

Various devices have been used in pipe reactors for providing high shear, but many of these (for example jets, mechanical mixers, oscillating flow) require high-energy input levels, which are expensive to run or involve relatively sensitive equipment. In many cases, high degrees of conversion are still not reached in a practical time span.

The inventors have realised that the transesterification reaction itself is quite fast (that is, it has a high rate constant) and that the time required to reach the desired level of completion is limited neither by the rate constant itself, nor simply by steric factors (reaction surface area of droplets) but by mass transfer factors and stoichiometric factors.

Mass transfer factors can be explained by considering a droplet of basic methanol surrounded by triglyceride at a temperature, for example around 60° C. Reaction on the surface of the droplets would take place very quickly creating a layer of methyl ester (biodiesel) and glycerine. There would result a sea of triglycerides surrounding a methyl ester (outside layer), glycerine (middle layer) and basic methanol droplet (central core). For the reaction to continue the methyl ester will have to diffuse into the surrounding triglycerides and the glycerine would have to be diluted continuously by the basic methanol from within the droplet's reducing core. Accordingly the reaction becomes limited by the rate of diffusion of reactants and reaction products. The inventors have realised that it is necessary to maintain a certain level of turbulence in the reactor for this transfer to be enhanced for long enough to drive the reaction to a high level of conversion.

When considering stoichiometric factors, the position of the equilibrium between the glyceride ester and the short chain alcohol ester (the biodiesel) is determined by the relative quantity of oil and short chain alcohol. In a continuous reaction in a pipe reactor, different stages in the pipe reactor represent different stages in the progress of the reaction. Later stages have lower quantities of short chain alcohol and oil. The inventors have realised that if the reaction volume from a later part of the reaction is mixed by backflow with the reaction volume from an earlier part of the reaction (an upstream part of the pipe reactor), the reactants may be diluted with reaction products (glycerol and short chain alcohol ester) which can adversely affect the position of the equilibrium and the rate of reaction.

A method is proposed of reacting a natural oil with a short chain alcohol in the presence of alkaline catalyst, in which a mixture of natural oil, short chain alcohol and alkaline catalyst is fed in one direction along a pipe reactor under transitional or turbulent conditions, so that the reactants are mixed in a direction normal to the flow direction, such that the time taken for 90% of the elements of fluid to pass through the reactor is within 20% of the mean residence time of reactant in the reactor.

Preferably, the time taken for 90% of the elements of fluid to pass through the reactor is within 15%, preferably within 10% of the mean residence time of reactant in the reactor. The skilled person will be aware as part of their common general knowledge how to determine mean residence time and the distribution of time taken for elements of fluid to pass through the reactor.

Further, an apparatus is proposed comprising a pipe reactor, a feed of natural oil, a feed of short chain alcohol and a feed of alkaline catalyst, the feed being arranged to feed the reactants in one direction along the pipe reactor, a turbulence generator being provided so that the reactants are fed in transitional or turbulent conditions, so that reactants are mixed in a direction normal to the flow direction, such the time taken for 90% of the elements of fluid to pass through the reactor is within 20% of the mean residence time of reactant in the reactor.

The short chain alcohol may be the same type of short chain alcohol as used in the esterification reaction of the present invention.

The alkaline catalyst preferably comprises potassium hydroxide or sodium hydroxide, or sodium or potassium methoxide. It may be supplied in powder or pellet form or in the form of a concentrated aqueous or alcoholic solution.

The relative quantities of the reactants can be at any suitable level; preferably the ratio by mass of short chain alcohol to natural oil is in the range 1:3 to 1:10, more preferably 1:3 to 1:6 and most preferably in the range 1:4 to 1:5.

The ratio by mass of alkaline catalyst in natural oil is suitably in the range 0.05% to 25%, preferably 0.5% to 5%.

Preferably, the alkaline catalyst and the short chain alcohol are mixed together before being mixed with the natural oil. A pre-prepared mixture of alkaline catalyst and alcohol may be obtained, for example from another site.

The pipe reactor may comprise any suitable design of reactor. It should have an inflow end and an outflow end, a flow direction being defined from the inflow end to the outflow end. It may have any suitable configuration. Preferably, it is parallel sided, though the flow cross section may vary across the length of the pipe reactor. Means may be provided for heating or cooling the pipe reactor. Preferably, the pipe reactor has a diameter in the range 2-1600 mm, although for commercial operation the diameter is typically in the range 12-500 mm. The pipe reactor may be comprised of a single length of pipe or a plurality of lengths of pipe connected together. It may have a substantially straight configuration or it may be curved. It may comprise bends or turns. A plurality of straight pipe sections connected by connecting means may be provided. Straight line pipe sections may be contained within a single structure for example an insulated structure of a vessel for containing heated fluid for heating the pipe reactor.

Preferably, plug flow maintenance in the transesterification pipe reactor is 80% or more.

"Plug flow maintenance' as used herein is defined by the following test.

Plug flow maintenance is measured between two defined points. Preferably the defined points are substantially near the inflow end and near the outflow end of the pipe reactor. They may be located just outside the pipe reactor.

The pipe reactor is provided with electrical conductivity measuring devices at the defined points. The length between the conductivity meters is preferably at least in the range 100 to 110% of the length of the pipe reactor.

To measure plug flow maintenance, a stable flow of reactants is preferably first established within the pipe reactor.

At time defined as t=0, a measured dose of one molar salt (sodium chloride) solution is injected into the flow. The quantity of salt solution injected is preferably such that it is sufficient to define a lamina of relatively narrow thickness (preferably about 1 cm), preferably extending in the direction normal to the flow direction across the whole width of the pipe reactor.

The width of the lamina of salt solution at the first defined point is measured by measuring the conductivity output from the first conductivity meter. The full width at half maximum of the conductivity peak is measured.

The width of the lamina at the second defined point is then measured by measuring the conductivity from the second conductivity meter. The full width at half maximum of the conductivity peak is measured.

Plug flow maintenance is defined as the ratio of the first measurement of the width of the lamina to the second measurement of the width of the lamina.

Preferably, the plug flow maintenance is greater than 80%, more preferably greater than 85% and most preferably greater than 90%.

If the plug flow maintenance is greater than 80%, intermixing of reacted products from one part of the pipe reactor with reactants from an upstream stage is kept to a sufficiently low level to allow the transesterification reaction to proceed quickly to a high level of conversion. Preferably, the level of conversion exceeds 95%, more preferably greater than 96.5%. The level of conversion can be measured by determining the quantity of natural oil remaining at the end of the reaction as a percentage of natural oil fed in, Q % and representing conversion as 100−Q %.

Preferably, the reactants flow through the transesterification pipe reactor in one direction in the sense that the flow is not an oscillating flow, as described in relation to the esterification pipe reactor.

The reactants are preferably placed under a pressure in the transesterification pipe reactor in excess of 0.5 bar gauge, more preferably in the range 1-10 bar gauge.

The reactants are preferably fed through the reactor at a linear bulk flow speed which is greater than 0.25 m/s and preferably less than 100 m/s. The speed should be sufficient that the flow is either turbulent or at the turbulent/laminar flow transition.

The person skilled in the art would be able to determine whether the flow within the pipe reactor is laminar, turbulent or at the turbulent/laminar flow transition.

It is found that a number of methods and structures may be used to ensure that the reactants pass along the pipe reactor under transitional or turbulent conditions and so that the reactants are mixed in a direction normal to the flow direction such that the time taken for 90% of the elements of fluid to pass through the reactor is within 20% of the mean residence time of reactant in the reactor.

Such constructions and methods may also be applied to achieve the desired maintenance of plug flow.

For example, the pipe reactor may comprise a plain pipe without any mixing elements. If the flow is maintained at a correct rate such that flow is either turbulent or at the transition between turbulent and laminar flow, and the pipe is of sufficient length, the required plug flow maintenance may be obtained.

Preferably, however, static mixing elements are present in the pipe reactor.

Preferably the static mixing elements are of a design which provides a higher level of deviation of the fluid flow path in a direction normal to the flow direction through the pipe reactor than in a direction parallel to the flow direction through the pipe reactor.

Suitable design of static mixer element can be obtained from Sultzer or Chemineer.

The degree of mixing can be represented by the power per unit weight of reactants. With the present invention the power per unit weight preferably exceeds 0.5 W/kg, being more preferably in the range 1 W/kg to 20 W/kg, more preferably more than 3 W/kg and preferably less than 15 W/kg.

The reactants flowing from the outflow end of the pipe reactor may be treated according to any known method to separate the biodiesel and other components.

Preferably, the natural oil, the short chain alcohol and the alkaline catalyst are mixed upstream of the transesterification pipe reactor.

Preferably, the flow of mixed natural oil, short chain alcohol and alkaline catalyst is turbulent when it enters the pipe reactor.

Turbulence may be generated by injecting a flow of short chain alcohol, optionally with alkaline catalyst dissolved therein, into a flow of natural oil, preferably at an angle (preferably approximately a right angle) to the direction of flow of the natural oil.

Means may be provided for heating the natural oil before it is mixed with the alkaline catalyst and short chain alcohol.

The temperature in the transesterification pipe reactor is preferably raised above ambient temperature. Preferably, it is in the range 40-120° C.

Static mixer elements may be present for at least part of the length of the transesterification pipe reactor. Static mixer elements are preferably present for at least the first 20% of the length, more preferably for at least the first 30% of the length.

Preferably, static mixer elements are present for at least the last 20%, more preferably for at least the last 30% of the length of the pipe reactor.

Preferably, there is a portion of the transesterification pipe reactor which has no mixer elements. This portion is preferably at least 20% and more preferably at least 30% of the length of the reactor. Preferably, the portion of the pipe reactor that has no mixer elements is displaced from the ends thereof.

It is found that, in a first stage of the reaction, where there is a very large quantity of unreacted natural oil, a high degree of mixing is beneficial for obtaining a high rate of reaction. In a middle section of the process, a substantial portion of the natural oil has been converted to mono- or diglycerides. These are found to have surfactant properties. This can enhance the mixing of the reactants in the middle part of the reaction. In a final part of the reaction, a substantial proportion of the natural oil has been converted to biodiesel and it is found that further mixing is beneficial.

Preferably, over 95%, more preferably over 96.5% by weight of natural oil is converted in a single pass through the pipe reactor. Preferably, there is no further transesterification reactor. Preferably, the residence time of the reactant in the pipe reactor is less than five minutes, more preferably less than 2.5 minutes, most preferably less than two minutes.

The transesterification pipe reactor may comprise a section comprising mixer elements that is located upstream of a point where short chain alcohol, alkaline catalyst or a mixture thereof is injected into the flow. This ensures that the flow is already turbulent at the point where the reactants are mixed, obtaining a high level of intermixing and reaction.

The present invention will be further described by way of example only with reference to the accompanying drawings, in which.

Figure 1:
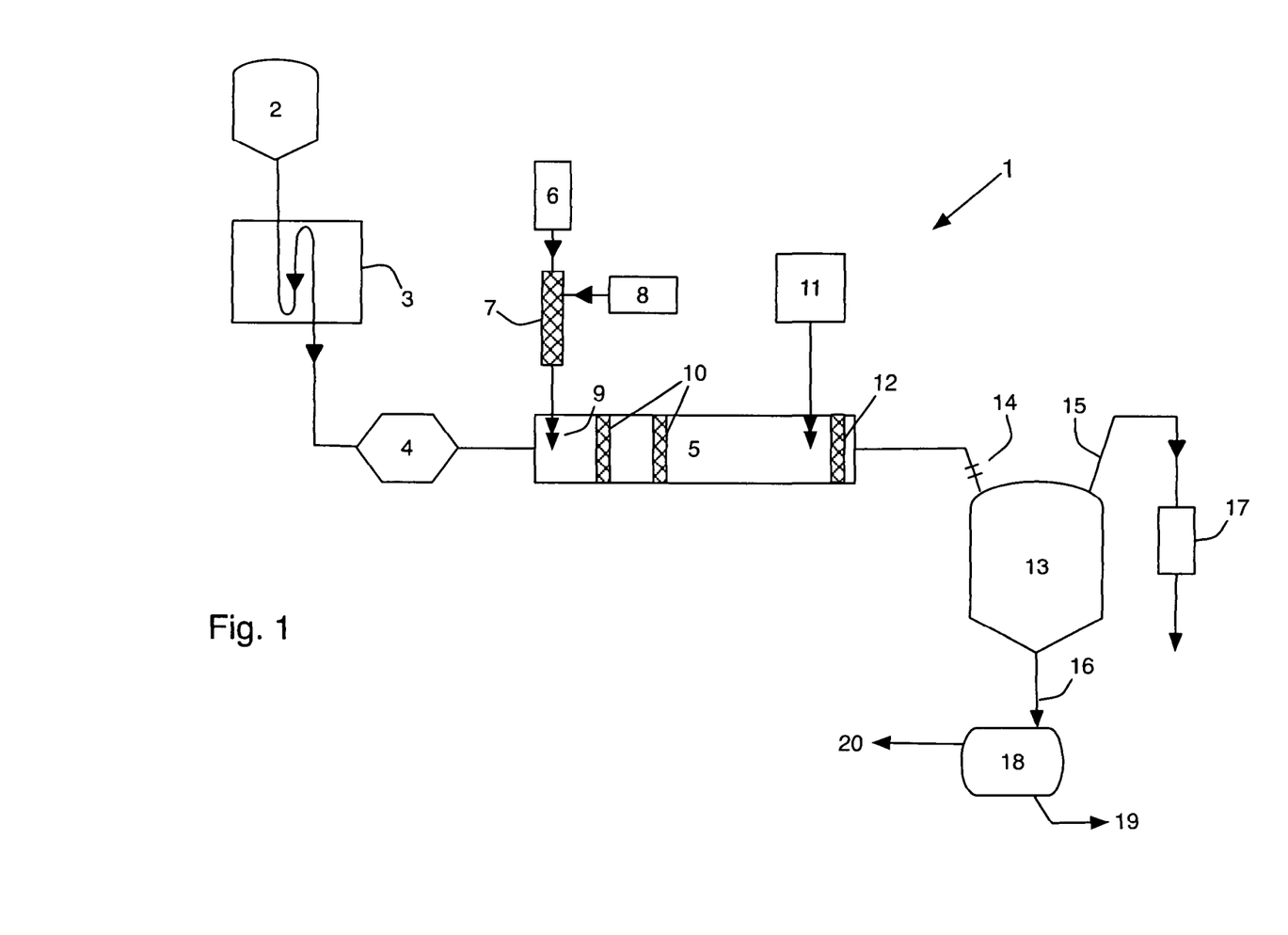
FIG. 1 is a schematic illustration of an apparatus for carrying out the process of the present invention.

FIG. 1 is a schematic view of an apparatus 1 for esterifying free fatty acid in natural oil. Components are shown schematically and not to scale. Details, such as pumps, valves etc are not shown except where they are required for an understanding of the invention. The person skilled in the art will be able to include conventional valves and pumps in accordance with their general knowledge.

The apparatus 1 comprises a tank 2 for storing a natural oil, such as sunflower oil. The natural oil is fed into a heater 3 where its temperature is raised to about 150° C. A pump 4 is provided for feeding the heated natural oil into a pipe reactor 5. The pump 4 can be any conventional pump and does not need to be made of acid resistant material, because no acid has been mixed with the oil at this stage. The feed of natural oil 2 may comprise natural oil which has been treated in the degumming apparatus 106 explained in relation to FIG. 2 below or it may comprise a feed, for example a tank, of natural oil obtained by any other means.

The pipe reactor 5 will be described further below.

Also fed into the pipe reactor is a mixture of short chain alcohol (in this case, methanol) and acid catalyst. The methanol is contained in a tank 6 and it is fed to a mixing device 7 where it is mixed with acid catalyst from the tank 8. At the same time, the mixture is placed under pressure and fed through a jet nozzle 9 into the flow of natural oil that is flowing through the pipe reactor. The natural oil is placed under a pressure in the range 1-10 bar gauge. The methanol and acid are fed by the device 7 at higher pressure than the oil so that they flow at high speed into the natural oil, obtaining a high degree of mixing. The jet nozzle 9 is configured to feed the mixture of methanol and acid in a direction that is generally normal to the bulk flow direction of natural oil through the pipe reactor 5. The methanol and acid are maintained at a temperature of less than 70° C., and normally at ambient temperature. For this reason, the mixing device 7 may be made of material that is capable of resisting acid at ambient temperature and does not need to be made of higher grade materials for resisting hot acid.

The pipe reactor 5 comprises a parallel sided cylindrical section tube is suitably made of a conventional engineering carbon steel. It is lined with an acid resistant PTFE layer. As it is made of a conventional engineering steel, it need not be very expensive. As it does not comprise moving parts, acid resistance can be imparted relatively easily with a lining material.

Static mixer elements 10 are provided at various stages in the pipe reactor to ensure a high degree of mixing. As the acidic methanol is relatively miscible with the natural oil, the static mixer elements typically provide sufficient mixing to obtain a high degree of reaction. Preferably, the mixer elements are of a type that provides a high degree of mixing in the direction normal to the bulk flow direction compared to mixing parallel to the flow direction. They may for example comprise KENICS™ KMX mixer elements.

An aqueous solution of potassium hydroxide is stored in a tank 11 and mixed into the pipe reactor near to the outflow end. Further static mixer elements 12 may be provided to ensure that the aqueous potassium hydroxide solution mixes with the natural oil. Sufficient potassium hydroxide solution is added to react with the acid catalyst and neutralise it.

The reactants from the pipe reactor 5 are then fed into a separator through a pressure reducing valve 14. The pressure reducing valve reduces the pressure of the reactants quickly to a level that is approximately ambient pressure. As the reactants coming out of the reactor are at a high temperature (about 130° C.), the rapid drop in pressure causes the methanol to flash evaporate. It is separated at vent 15 from the top of the separator 13. The liquid phase 16 is connected at the bottom. Vaporised methanol is collected and cooled in a condenser 17 and may be recycled to the methanol tank 6. Heat collected in the methanol condenser 17 may be fed to the heater 3.

Heat of condensation of vaporised methanol collected in the apparatus 17 can be used to heat natural oil at an earlier stage in the process. For example, it may be used in the heater 3 or it may be used in a separate heater 105 as explained in relation to FIG. 2.

A further separator 18 is provided in which the natural oil is allowed to stand for sufficient time for the aqueous layer (comprising the aqueous salt solution produced by reaction of the potassium hydroxide and the acid catalyst) to separate. The aqueous layer is removed at 19 and disposed of. The treated natural oil is collected at 20 for further treatment, for example transesterification as explained in relation to FIG. 2 below.

Figure 2:
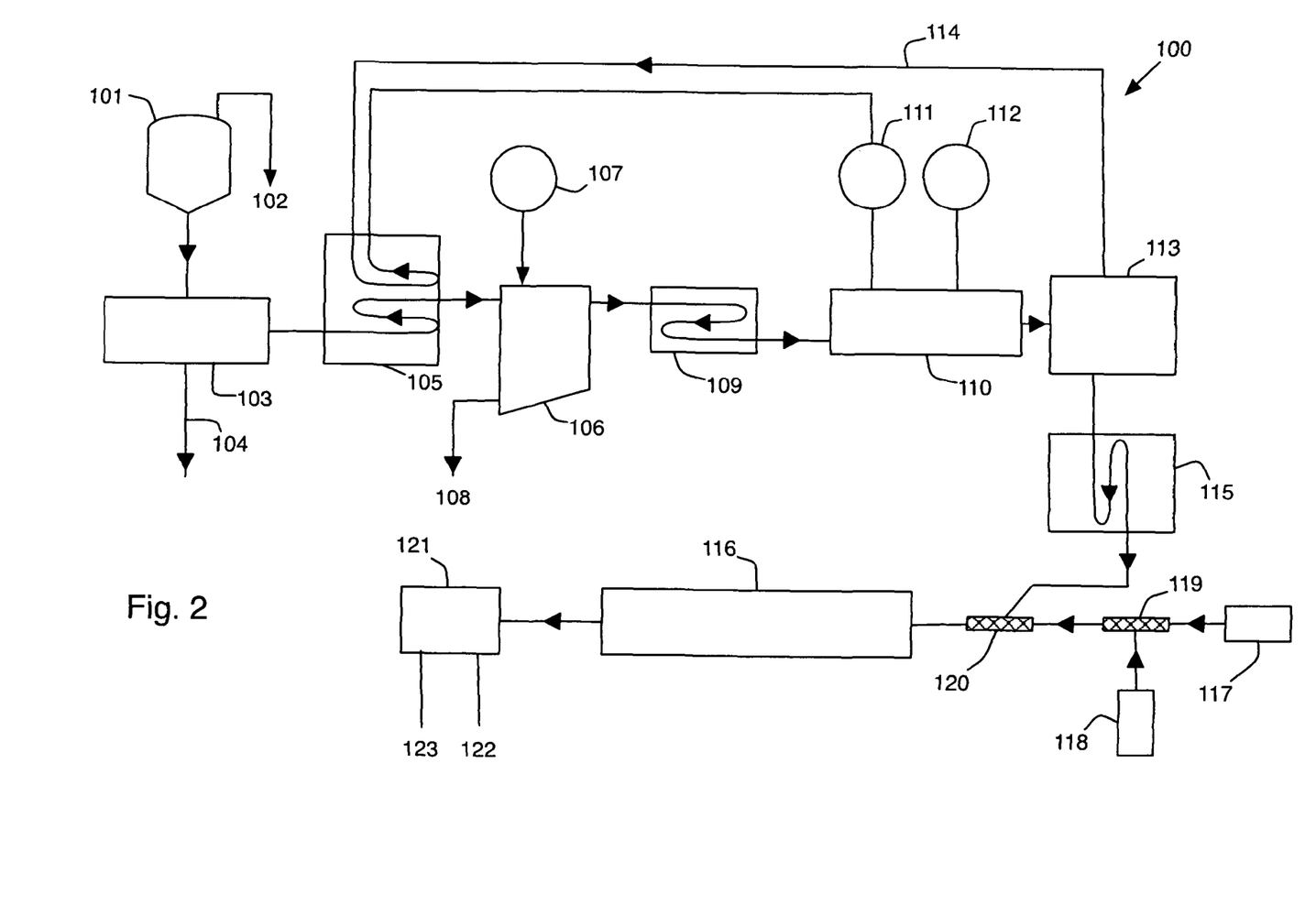
FIG. 2 is a schematic plan of a plant for synthesis of biodiesel from a raw material.

FIG. 2 is a schematic view of a complete plant for biodiesel synthesis from materials such as nuts or seeds. The nuts or seeds are initially crushed and pressed in a crusher 101. Suitable designs of crusher or press are the known to the person skilled in the art. The crushed and pressed seed material is rejected at 102 and may be disposed of, for example by burning to generate heat. A raw natural oil is obtained and is passed into a hexane extractor 103, where hexane is used to extract certain impurities. The impurities are rejected at 104 and the partially treated raw natural oil is fed to heat exchanger 105, corresponding to the heat exchanger 3 of FIG. 1. The heat exchanger 105 raises the temperature of the partially treated raw natural oil to about 100° C. and it is then fed into a degumming plant 106.

Suitable designs of hexane extractor will be known to the person skilled in the art. Suitable designs of degumming plant are known to the person skilled in the art. In the degumming plant 106, phosphoric acid, stored in a tank 107 is dosed into the heated partially treated raw natural oil to polymerise phospholipids which are precipitated and collected at 108 for disposal. Secondary treated natural oil is then collected at the top of the vessel and fed to a second heat exchanger 109 where the temperature is raised to 130° C.

The heated secondary treated raw natural oil is fed to an apparatus 110 for esterifying fatty acid in the natural oil, which is according to the present invention and corresponds to the pipe reactor 5 shown in FIG. 1. Connected to the esterification apparatus 110 are a storage tank 111 for methanol and a storage tank 112 for an aqueous solution of potassium hydroxide, which correspond respectively to storage tanks 6 and 11 of FIG. 1. The mixing device 7 and the storage tank 8 for acid catalyst shown in FIG. 1 have been omitted from FIG. 2 for clarity. Operation of the esterification apparatus 110 is as described above in relation to FIG. 1.

The final treated raw natural oil obtained is then fed into a separator 113 corresponding to the separator 13 of FIG. 1. The short chain alcohol is removed in the separator 113 as a vapour.

The vapour is transferred by a line 114 and condensed in a condenser corresponding to condenser 17 of FIG. 1, the heat being used in the heat exchanger 105 as shown schematically in FIG. 2. Other arrangements for transferring the heat of condensation of the methanol may be used. However, it is beneficial that the heat exchange to remove heat from the vapourised methanol is achieved by contacting it with the raw natural oil which is at ambient temperature. Because these fluids have a very great temperature difference, the heat exchange is rapid and efficient. The cooled methanol is then returned to the storage tank 111.

The natural oil will be typically cooled by the vapourisation of the methanol to about 50-60° C. and needs to be heated again in a third heat exchanger 115, where it is heated to a temperature of 130° C. The heated oil is then fed into a pipe reactor 116.

Alkaline catalyst is fed from a tank 117 and mixed in a mixer 119 with short chain alcohol from a tank 118. This mixture is then mixed with the finally treated natural oil in a further mixing stage 120, the reactants then being fed into a pipe reactor 116. The mixer 119, mixing stage 120 and pipe reactor 116 are described further below with respect to FIG. 3.

A mixture of biodiesel and glycerine is obtained in the pipe reactor 116 and is then fed to a separator 121 where glycerine and used alkaline catalyst are separated and rejected at 122 for disposal, burning or reuse as appropriate. Finally, a high quality biodiesel is obtained at 123.

Figure 3:
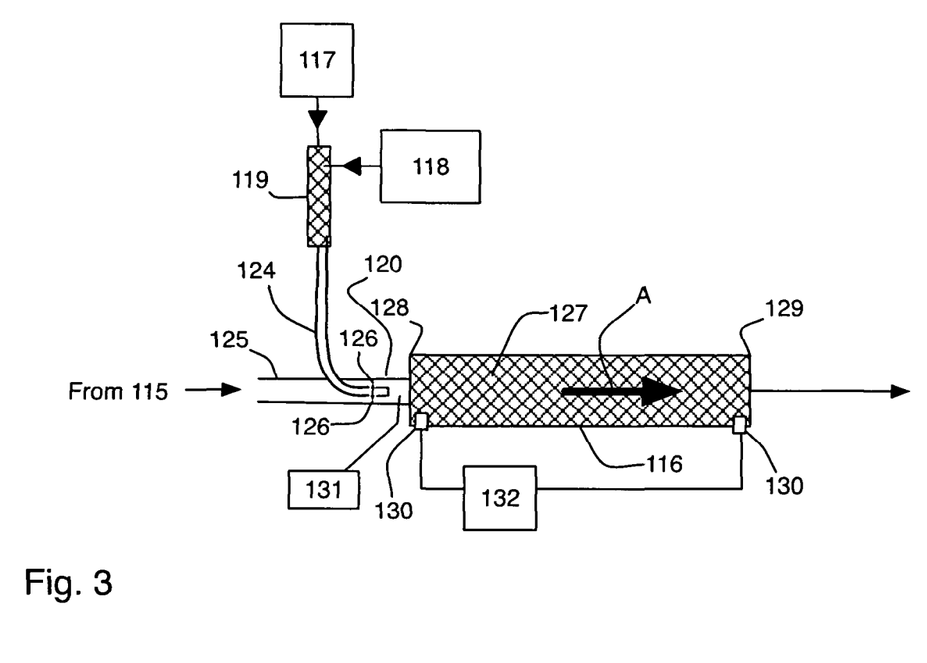
FIG. 3 is a schematic illustration of a transesterification apparatus for use with the present invention.

The transesterification reactor of FIG. 3 shows the components 117, 118, 120, 119 and 116 in more detail.

Natural oil is fed through pipe 125 from the heater 115.

Alkaline catalyst is fed from the tank 117 and mixed in a mixer 119 with short chain alcohol from the tank 118.

The mixer 119 also comprises a pump for feeding the mixture of short chain alcohol and alkaline catalyst under pressure through a tube 124 into the tube 125. The tube 124 terminates in jet nozzles 126 directed generally normal to the direction of flow through the pipe 125. This generates turbulence in the pipe 121. The turbulent mixture of natural oil, short chain alcohol and alkaline catalyst is fed into the pipe reactor 116.

At least in the first part, the pipe reactor 116 comprises mixing elements 127 which are of a configuration such that they cause greater mixing in a direction normal to the direction of flow (indicated by arrow A) through the pipe reactor 116 than mixing in a direction parallel to the flow direction A.

The pipe reactor 116 has an input end 128 and an output end 129. At or very close to the input end 128 and output end 129, conductivity meters 130 are provided.

A dosing means 131 is provided for dosing the apparatus with a salt solution, so that the plug flow maintenance in the pipe reactor 116 between the input and output ends 128 and 129 can be measured.

At the output end 129, reaction products comprising biodiesel, glycerol and small quantities of un-reacted components are fed to further treatment (as described in FIG. 2).

A controller 132 is provided for controlling and monitoring the output of the conductivity meters 130.

The dosing device 131 can be used to inject into the flow in pipe 125 a quantity of one molar sodium chloride in such a quantity to form a lamina at least one centimeter wide in the direction normal to the flow direction A.

The conductivity meters 130 can then be used in conjunction with the controller 132 to measure the plug flow maintenance across the length of the reactor by the method described above.

The invention claimed is:

1. A method for the synthesis of biodiesel comprising a first step esterifying free fatty acid in natural oil, comprising heating the natural oil to a first temperature above a reaction temperature, feeding the heated natural oil into an acid-resistant pipe reactor, providing a mixture of acid catalyst and short chain alcohol at a second temperature below the reaction temperature, and feeding the mixture of acid catalyst and short chain alcohol at the second temperature into the natural oil in the acid-resistant pipe reactor, pumping the heated natural oil and the mixture of acid catalyst and short chain alcohol through the pipe reactor from the inflow end to the outflow end to cause the short chain alcohol and free fatty acid to react at the reaction temperature to form an ester within the natural oil, thereby forming a treated natural oil, and a second step of providing a mixture of alkaline catalyst and short chain alcohol, mixing the treated natural oil with the mixture of alkaline catalyst and short chain alcohol, and feeding a mixture of natural oil, short chain alcohol and alkaline catalyst in one direction along a second pipe reactor under transitional or turbulent conditions, thereby synthesising biodiesel by transesterification.

2. A method according to claim 1 in which the reaction temperature is in the range 100° C. to 200° C.

3. A method according to claim 2 in which the first temperature is higher than the reaction temperature by a temperature difference in the range 10° C. to 50° C.

4. A method according to claim 3 in which the second temperature is less than 70° C.

5. A method according to claim 1 in which the mixture of acid catalyst and short chain alcohol is fed into the natural oil in the acid-resistant pipe reactor at a pressure greater than 0.5 bar gauge.

6. A method according to claim 1 in which the mixture of acid catalyst and short chain alcohol is fed into the natural oil in the acid-resistant pipe reactor at an angle to the direction of flow of the natural oil.

7. A method according to claim 1, further comprising reducing the pressure of reactants at an outlet of the acid-resistant pipe reactor to remove excess short chain alcohol by evaporation.

8. An apparatus for synthesis of biodiesel, comprising an apparatus for esterifying free fatty acid in natural oil, comprising a heater for heating natural oil to a first temperature above a reaction temperature, a feed for feeding the heated natural oil into an acid-resistant pipe reactor, a feed for a mixture of acid catalyst and short chain alcohol at a second temperature below the reaction temperature, the feed for the mixture of acid catalyst and short chain alcohol being configured to feed the mixture into the natural oil in the acid-resistant pipe reactor, a pump for pumping the heated natural oil and the mixture of acid catalyst and short chain alcohol through the pipe reactor from the inflow end to the outflow end to cause the short chain alcohol and free fatty acid to react at the reaction temperature to form an ester within the natural oil, thereby forming a treated natural oil, and an apparatus for synthesising biodiesel by transesterification comprising a second pipe reactor, a feed for the treated natural oil, a feed for a mixture of short chain alcohol and alkaline catalyst, the feed being arranged to feed the reactants in one direction along the pipe reactor, and a turbulence generator being provided so that the reactants are fed in transitional or turbulent conditions.

9. An apparatus according to claim 8 in which the heater is configured to heat the natural oil to a first temperature providing reaction temperature reaction temperature in the range 100° C. to 200° C.

10. An apparatus according to claim 9 in which the heater is configured to heat the natural oil to a first temperature that is higher than the reaction temperature by a temperature difference in the range 10° C. to 50° C.

11. An apparatus according to claim 10 in which the feed for the mixture of acid catalyst and short chain alcohol is configured to provide a second temperature of less than 70° C.

12. An apparatus according to claim 8 in which the feed for the mixture of acid catalyst and short chain alcohol is configured to feed the mixture into the natural oil at a pressure greater than 0.5 bar gauge.

13. An apparatus according to claim 8 in which the feed for the mixture of acid catalyst and short chain alcohol is configured to feed the mixture into the natural oil in the acid-resistant pipe reactor at an angle to the direction of flow of the natural oil.

14. An apparatus according to claim 8, further comprising a pressure reducing valve for reducing the pressure of reactants at an outlet of the acid-resistant pipe reactor to remove excess short chain alcohol by evaporation.

15. An apparatus according to claim 8, in which the acid-resistant pipe reactor includes a corrosion-resistant lining.

16. A method according to claim 2 in which the reaction temperature is in the range 120° C. to 170° C.

17. A method according to claim 1 in which the first temperature is higher than the reaction temperature by a temperature difference in the range 10° C. to 50° C.

18. A method according to claim 3 in which the first temperature is higher than the reaction temperature by a temperature difference in the range 20° C. to 40° C.

19. A method according to claim 3 in which the second temperature is less than 60° C.

20. A method according to claim 1 in which the mixture of acid catalyst and short chain alcohol is fed into the natural oil in the acid-resistant pipe reactor at a pressure in the range 1 to 20 bar gauge.

21. A method according to claim 1, wherein the reactants are mixed in the second pipe reactor in a direction normal to the flow direction, such that the time taken for 90% of the reactants to pass through the second pipe reactor is within 20% of the mean residence time of reactants in the second pipe reactor.

22. An apparatus according to claim 8, wherein the reactants are mixed in a direction normal to the flow direction, such the time taken for 90% of the reactants to pass through the second pipe reactor is within 20% of the mean residence time of reactants in the reactor.

23. A method for the synthesis of biodiesel, including:
a first step of esterifying free fatty acid in natural oil, comprising: heating the natural oil to a first temperature above a reaction temperature; feeding the heated natural oil into an acid-resistant pipe reactor; providing a mixture of acid catalyst and short chain alcohol at a second temperature below the reaction temperature; said second temperature being below 70° C.; feeding the mixture of acid catalyst and short chain alcohol, at the second temperature, into the natural oil in the acid-resistant pipe reactor; and pumping the heated natural oil and the mixture of acid catalyst and short chain alcohol through the pipe reactor from an inflow end to an outflow end to cause the short chain alcohol and free fatty acid to react at the reaction temperature, said reaction temperature being in the range of 100° C. to 200° C., to form a treated natural oil having an ester within the natural oil; and
a second step of transesterification, comprising: providing a mixture of alkaline catalyst and short chain alcohol; mixing the treated natural oil with the mixture of alkaline catalyst and short chain alcohol; and feeding a mixture of natural oil, short chain alcohol and alkaline catalyst in one direction along a second pipe reactor under transitional or turbulent conditions, thereby synthesising biodiesel by transesterification.

* * * * *